US005599301A

United States Patent [19]
Jacobs et al.

[11] Patent Number: 5,599,301
[45] Date of Patent: Feb. 4, 1997

[54] MOTOR CONTROL SYSTEM FOR AN AUTOMATIC CATHETER INFLATION SYSTEM

[75] Inventors: James M. Jacobs, Mountain View; Joseph A. O'Donnell, Escondido, both of Calif.

[73] Assignee: Advanced Cardiovascular Systems, Inc., Santa Clara, Calif.

[21] Appl. No.: 156,268

[22] Filed: Nov. 22, 1993

[51] Int. Cl.$^6$ ................................... A61M 29/00
[52] U.S. Cl. .......................................... 604/65
[58] Field of Search ................. 604/100, 96, 30–34, 604/49, 53, 65–67; 128/DIG. 13, DIG. 12

[56] References Cited

U.S. PATENT DOCUMENTS

| | | |
|---|---|---|
| 3,623,474 | 11/1971 | Heilman . |
| 3,698,381 | 10/1972 | Federico et al. . |
| 3,701,345 | 10/1972 | Heilman et al. . |
| 3,720,199 | 3/1973 | Rishton et al. . |
| 4,006,736 | 2/1977 | Kranys et al. . |
| 4,056,043 | 11/1977 | Sriramamurty et al. . |
| 4,106,002 | 8/1978 | Hogue, Jr. . |
| 4,321,014 | 3/1982 | Eburn, Jr. et al. . |
| 4,332,254 | 6/1982 | Lundquist . |
| 4,370,982 | 2/1983 | Reilly . |
| 4,439,185 | 3/1984 | Lundquist . |
| 4,439,186 | 3/1984 | Kuhl . |
| 4,444,335 | 4/1984 | Wood et al. . |
| 4,493,704 | 1/1985 | Beard et al. . |
| 4,576,181 | 3/1986 | Wallace . |
| 4,583,917 | 4/1986 | Shah . |
| 4,583,974 | 4/1986 | Kokernak . |
| 4,608,994 | 9/1986 | Ozawa et al. . |
| 4,610,256 | 9/1986 | Wallace . |
| 4,651,738 | 3/1987 | Demer et al. . |
| 4,654,027 | 3/1987 | Dragan et al. . |
| 4,655,749 | 4/1987 | Fischione . |
| 4,677,980 | 7/1987 | Reilly et al. . |
| 4,677,982 | 7/1987 | Llinas et al. . |
| 4,694,409 | 7/1987 | Lehman . |
| 4,723,938 | 2/1988 | Goodin et al. . |
| 4,743,230 | 5/1988 | Nordquest . |
| 4,758,223 | 7/1988 | Rydell . |
| 4,781,192 | 11/1988 | Demer . |
| 4,795,431 | 1/1989 | Walling . |
| 4,796,606 | 1/1989 | Mushika . |
| 4,808,165 | 2/1989 | Carr . |
| 4,832,692 | 5/1989 | Box et al. . |
| 4,838,864 | 6/1989 | Peterson . |

(List continued on next page.)

FOREIGN PATENT DOCUMENTS

| | | |
|---|---|---|
| WO90/04987 | 5/1990 | WIPO . |
| WO90/11040 | 10/1990 | WIPO . |
| WO92/06735 | 4/1992 | WIPO . |
| WO92/15359 | 9/1992 | WIPO . |

OTHER PUBLICATIONS

Paul H. Lange, M.D., Chapter 8, *Diagnostic and Therapeutic Urologic Instrumentation*.

John T. Isaacs, Ph.D. and Gary D. Steinberg, M.D., *A Guide to the Physiology of the Prostate*, Contemporary Urology, May 1990.

Christopher M. Dixon, M.D. and Herbert Lepor, M.D., *Lasers Add a Glow to the Search for BPH Therapies*, Contemporary Urology, Oct. 1993.

*Primary Examiner*—Manuel Mendez
*Attorney, Agent, or Firm*—Fulwider Patton Lee & Utecht, LLP

[57] ABSTRACT

A motor controller for providing a constant rate of change of pressure during inflation and deflation of an expandable member of a catheter for use in a body lumen by an automated inflation system is disclosed. The system conforms the rate of change of pressure to a set point value by means of a feedback loop controller, and makes possible consistent inflations and deflations using an automated system regardless of variations in catheter volume and compliance characteristics. Safety features such as maximum pressure and balloon rupture alarms are also disclosed.

33 Claims, 7 Drawing Sheets

U.S. PATENT DOCUMENTS

| | | |
|---|---|---|
| 4,854,324 | 8/1989 | Hirschman et al. . |
| 4,911,695 | 3/1990 | Lindner . |
| 4,919,121 | 4/1990 | Rydell et al. . |
| 4,929,238 | 5/1990 | Baum . |
| 4,940,459 | 7/1990 | Noce . |
| 4,944,726 | 7/1990 | Hilal et al. . |
| 4,952,928 | 8/1990 | Carroll et al. . |
| 4,985,015 | 1/1991 | Obermann et al. . |
| 5,004,472 | 4/1991 | Wallace . |
| 5,007,904 | 4/1991 | Densmore et al. . |
| 5,009,662 | 4/1991 | Wallace et al. . |
| 5,015,233 | 5/1991 | McGough et al. . |
| 5,019,041 | 5/1991 | Robinson et al. . |
| 5,021,046 | 6/1991 | Wallace . |
| 5,047,015 | 9/1991 | Foote et al. . |
| 5,057,078 | 10/1991 | Foote et al. . |
| 5,084,060 | 1/1992 | Freund et al. . |
| 5,135,488 | 8/1992 | Foote et al. . |
| 5,152,776 | 10/1992 | Pinchuk . |
| 5,163,904 | 11/1992 | Lampropoulos et al. . |
| 5,201,753 | 4/1993 | Lampropoulos et al. . |
| 5,215,523 | 6/1993 | Williams et al. . |
| 5,273,537 | 12/1993 | Haskvitz et al. . |

MOTOR CONTROL SYSTEM FOR AN AUTOMATIC CATHETER INFLATION SYSTEM

BACKGROUND OF THE INVENTION

This invention generally relates to inflation devices used in medical procedures, and more particularly, to automated inflation devices having control systems suitable for controlling the inflation and deflation of catheter balloons used in procedures within a body lumen such as a blood vessel. Such procedures include, for example, vascular procedures such as angioplasty for restoring patency of a blood vessel.

Dilatation balloon catheters have been used in increasing numbers in angioplasty procedures to dilate or enlarge body lumens such as blood vessels (including coronary and peripheral arteries) that have been partially or almost completely blocked by stenosis (a narrowing of the lumen due to injury or disease). In addition to vascular procedures such as dilatation of the coronary and peripheral arteries, angioplasty procedures have been used to treat stenoses in other lumens, such as urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the stenosis. Subsequently, a guidewire and a dilatation catheter having an inflatable balloon on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the stenosis to be dilated, and is then advanced beyond the stenosis. Thereafter, the dilatation catheter is advanced over the guidewire until the dilatation balloon is located across the stenosis.

Once in position across the stenosis, the balloon of the dilatation catheter is filled with radiopaque liquid at relatively high pressures (e.g., generally greater than about 4 atmospheres) and is inflated to a predetermined size, preferably the same as the inner diameter of the artery at that location. The inflated balloon radially compresses the atherosclerotic plaque and/or other deposits comprising the stenosis against the inside of the artery wall to thereby dilate the lumen of the artery and allow blood to flow freely therethrough. In a typical PTCA procedure, the balloon is inflated and deflated several times, with the pressure maintained for several seconds during each inflation, until the desired patency in the blood vessel is obtained. The balloon is then deflated so that the dilatation catheter can be removed and blood flow resumed through the dilated artery.

To inflate or deflate the balloon, the physician typically uses an inflation system such as a syringe connected to the catheter and in fluid communication with the interior of the balloon. The physician uses one hand to grasp the syringe body and the other hand to actuate the plunger to pressurize and to depressurize the inflation fluid. Syringe-type inflation systems of the type described are manufactured and sold by Advanced Cardiovascular Systems, Inc. of Santa Clara, Calif. under the trademark INDEFLATOR.

There are some drawbacks associated with a manual inflation procedure such as the one described. For example, each time the physician wants to adjust or change the location of the balloon in the artery, she must use her hand alternatingly on the proximal end of the catheter for maneuvering the balloon to the desired location, and on the inflation device for pressurizing or depressurizing the balloon. Rather than switching hands between the balloon catheter and the inflation device, it is desirable for the physician to be able to simultaneously control the inflation pressure and the location of the balloon in the artery. This simultaneous control of position and balloon inflation pressure is not possible for a single physician using present manual inflation procedures.

Another drawback of manual inflation systems is that the physician may experience hand fatigue as a result of operating an inflation device for several inflation and deflation cycles, each lasting several seconds, during an angioplasty procedure. Additionally, manual inflation devices are typically bulkier than dilatation balloon catheters, and the presence of such a bulky instrument is preferably to be avoided in the immediate area of an angioplasty procedure.

In recent years, automated inflation devices have become known, including microprocessor controlled units wherein a microprocessor provides control signals to a drive unit which advances or retracts a syringe for the purpose of inflating or deflating a balloon catheter. The drive unit can be made to follow a predetermined pressure output pattern, based on the inflation pressure detected by a pressure transducer in fluid communication with the radiopaque inflation media, and an internal clock. Alternatively, inflation devices have been designed for manual activation, but which are monitored and incorporate a unit that displays inflation pressure and time values for example.

However, these conventional automated devices have limitations. For example, they do not take into account variations in individual catheter volume, nor do they take into consideration individual catheter compliance characteristics. As a consequence, differing inflation characteristics between individual catheters (which in manual inflation systems can be sensed and compensated for somewhat by the physician) can be a result. For example, either slower or faster inflation and deflation of individual catheters is one result. Depending on the attributes of the particular catheter, differing time verses pressure plots may be obtained, even between catheters having the same balloon volume. This is not desirable, as uniformity of performance is important in the equipment used in angioplasty. Particularly in PTCA procedures, where the consequences of a miscalculation on the part of the physician as to the equipment's effect on the coronary vasculature can be life-threatening, dependably uniform performance is essential.

Another problem with prior automated inflation devices is that they may over-control the inflation process, or under-control it. For example, equipment that automatically pressurizes the catheter according to a predetermined pattern does not provide feedback to the physician regarding the treatment. Clinical parameters such as arterial wall compliance and catheter compliance may be masked by the system such that the physician cannot sense them and control the procedure in response to such clinical parameters. Thus, inflation times and pressures may not be accurately controlled by the physician as treatment is taking place. Alternatively, in systems that merely monitor the inflation of the balloon inflation times and rates, these parameters can vary due to individual catheter compliance characteristics. Although the physician can sense these differences in system response, and compensate somewhat for them, it would be desirable to eliminate the differences in system response due to individual catheter characteristics inherent in manual systems, including monitored manual systems.

What has been needed and heretofore unavailable is an automated inflation system that frees the physician from the difficulties of manual inflation, but accounts for individual differences in balloon catheters, both as to fluid volume capacity and as to compliance characteristics. Such a system would be able to compensate for individual differences between catheters, so that catheter inflation and deflation characteristics are kept uniform from catheter to catheter, even though the catheters used with the system may have different individual properties. Nevertheless the automated inflation control system should not take ultimate control of the procedure from the physician. The present invention fulfills this need.

SUMMARY OF THE INVENTION

The invention is directed to an automatic inflation/deflation device for a catheter system for use in a body lumen of a patient. The system senses and controls the rate of change of pressure within an inflation lumen and inflatable member of a catheter, such that the inflatable member is inflated or deflated by fluid pressurized at a predetermined or preselected rates of increasing or decreasing pressure provided by a powered fluid pump. Sensing and controlling the rate of change of pressure of the inflation fluid media within the catheter system eliminates differences in catheter inflation characteristics due to differences in system volume and compliance.

In controlling the inflation or deflation of the inflatable member of a catheter, the speed of a powered fluid drive is varied in response to a sensed rate of change of pressure in the system, to conform the rate of change of pressure to a preselected rate. The rate can be varied by the user, by manipulation of selector dials. Thus the inflation of the catheter expandable member can be made to be predictable and uniform during inflation and deflation regardless of individual differences in system volume or compliance. However, in an automated system according to the present invention the physician controls inflation and deflation by means of a control switch unit, thus retaining absolute control over the procedure.

The automated inflation/deflation system of the present invention includes a catheter having an inflatable member near its distal end, and at least one inflation lumen therein providing fluid communication between a proximal end of the catheter and the inflatable member. The catheter is connected to a powered fluid pump for pressurizing contrast fluid in the inflation lumen. In fluid communication with the inflatable member of the catheter is a fluid pressure sensor for measuring pressure in said inflatable member. Coupled to the powered fluid pump and the pressure sensor is a controller for controlling the rate of change of fluid pressure by varying the pump speed, based upon the sensed pressure at the pressure sensor location. The controller includes a microprocessor, and including a means for storing a predetermined or set point rate of change of pressure information, as well as a means for comparing sensed pressure information with the set point or reference rate of change of pressure information and adjusting the motor speed to conform the rate of change of pressure to the stored reference value.

The controller is a closed loop electronic feedback device, and alternatively to a microprocessor controlled type that processes digital information, a circuit that processes analog information could be used. If a digital electronic system is employed, analog to digital converters and digital to analog converters may be employed as are known in the art. The pressure is continuously monitored at uniform time intervals and the rate of change of pressure continuously measured at those same increments of time. The motor speed is adjusted in response to an error signal generated based upon comparison of the measured rate of change of pressure to the set point or reference value at each time increment during inflation and deflation, and the cycle repeats. This control system conforms the rate of pressure change to the desired rate of pressure change. The controller can be adapted to receive information from a user interface, so that a user (for example a physician) can enter information such as a desired rate of change of pressure.

When the control switch is activated the rate of change of fluid pressure is conformed to the set-point value, and when the control switch is not activated the fluid drive motor is simply stopped. The physician can monitor the compliance of the body lumen being dilated by observation of the pressure drop in the system. Alternatively, the system can be made to conform the rate of change of pressure to a zero value when the control switch unit is not activated for inflation or deflation.

Thus the controller is simple in design and is inexpensive to manufacture and to use. A physician using the device simply actuates a switch to inflate or deflate the inflatable member of a catheter. A user need not concern herself with the variations in volume and compliance characteristics between catheters. The user can preselect set point values for inflation rate of change of pressure and deflation rate of change of pressure.

These and other features and advantages of the invention will become more apparent from the following detailed description, taken in conjunction with the accompanying exemplary drawings.

DETAILED DESCRIPTION OF THE PREFERRED EMBODIMENTS

Figure 1:
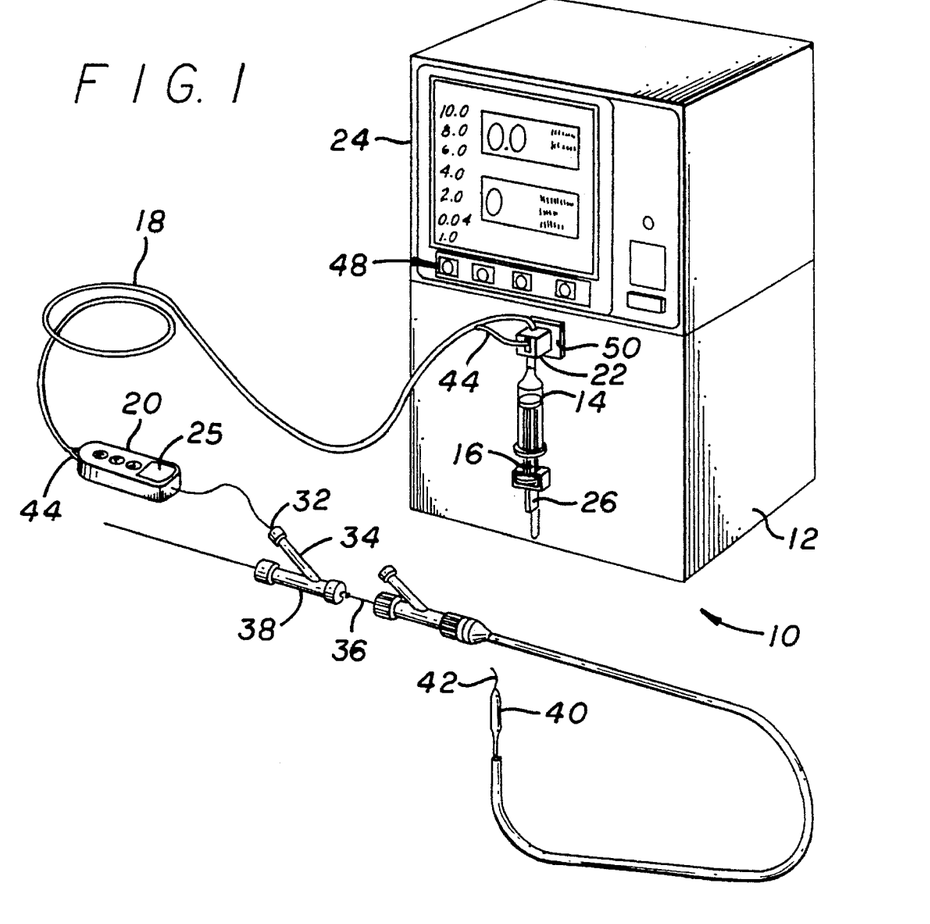
FIG. 1 is a schematic representation of an automated inflation/deflation system embodying features of the invention.

As shown in FIG. 1 for purposes of illustration, the invention is embodied in an automated inflation/deflation system 10. The automated inflation/deflation system generally includes an electromechanical drive unit 12, a fluid chamber 14 with a plunger 16, a length of connecting tubing 18, a control switch unit 20, a pressure transducer 22, and a display unit 24.

Electromechanical motor drive unit 12 incorporates an electric motor (not shown), which in a currently preferred embodiment is a DC servo motor. Other types of electric motors can be used, for example a stepper motor. As will be apparent to one skilled in the art, an appropriate gear train or other means can be used to adapt a wide variety of motors to this application. Alternatively, a hydraulic motor, a pneumatic motor, or the like, combined with electromechanical or mechanical pressure monitoring control means could be used in connection with the automatic inflation system 10. Whatever the specific type of motor used, electromechanical motor drive unit 12 typically has a moveable arm 26, conventionally driven by the motor, that is capable of directing the movement of another element, such as by pushing or pulling, that it may come in contact with. Arm 26 is connected to a plunger 16 of a fluid chamber 14. Fluid chamber 14 and plunger 16 may be formed of a conventional syringe/plunger combination with an O-ring or quad seal or with a rolling diaphragm seal for reduced friction. As will be apparent to one skilled in the art, other suitable means that can pressurize (and depressurize) and eject (or retract) a quantity of fluid may also be used.

As arm 26 forces plunger 16 inside fluid chamber 14, the inflation fluid inside fluid chamber 14 is pressurized, and is directed out of a fluid chamber outlet 28. The reverse movement of arm 26 reduces the pressure of the inflation fluid. A length of tubing 18 is connected at its proximal end 30 to outlet 28 and its distal end 32 is connected to the inflation lumen 34 of a balloon dilatation catheter 36. Inflation lumen 34 extends from the proximal end 38 of dilatation catheter 36 and is in fluid communication with the interior of an expandable member comprising a balloon 40 located at or near the distal end 42 of dilatation catheter 36. Accordingly, tubing 18 provides fluid communication between the interior of balloon 40 and the inflation fluid inside fluid chamber 14.

The control switch unit 20 activates motor drive unit 12 so that arm 26 of motor drive unit 12 applies force on plunger 16 of fluid chamber 14 and pressurizes or depressurizes the inflation fluid inside fluid chamber 14. Upon pressurization, the inflation fluid travels inside tubing 18 and flows into balloon 40 via the inflation lumen 34 of dilatation catheter 36. As can be seen, control switch unit 20 is mounted on the tubing 18 at or near distal end 32 of the tubing and in close proximity with proximal end 38 of dilatation catheter 36. This location makes control switch unit 20 easily accessible to the physician's hand used for grasping the proximal end 38 of dilatation catheter 36 for maneuvering it inside the patient's vasculature until balloon 40 is properly positioned at the site of the stenosis. Once balloon 40 is properly situated at the site of the stenosis, the physician may use the same hand to activate control switch unit 20 to effectuate the inflation of balloon 40 without losing control of the proximal end of dilatation catheter 36 and the location of balloon 40. Of course the physician could use the other hand to actuate the control switch unit. Also, whenever rapid deflation of balloon 40 is necessary, control switch unit 20 may easily be activated by the physician.

Control switch unit 20 may incorporate a rocker switch, a slide switch, a rotary switch, a pressure sensitive switch with tactile feedback, a non-electrical pneumatic control switch, a variable resistance element, or any other type of switch that may activate and deactivate motor drive unit 12. More than one control switch may be incorporated in the control switch unit.

Figure 2:
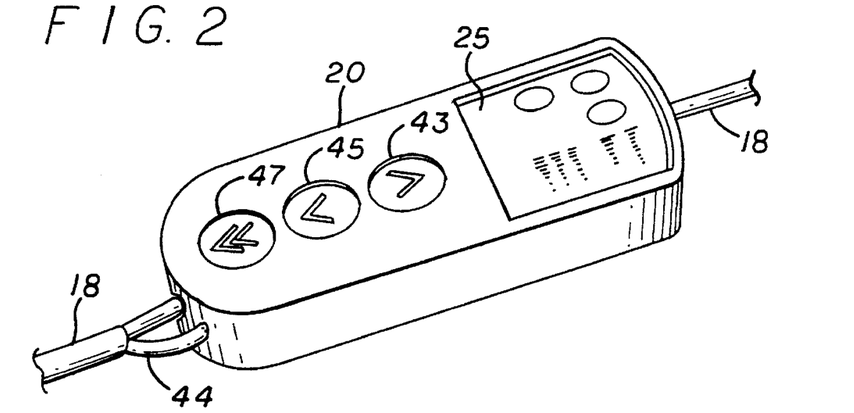
FIG. 2 is a schematic representation of a portion of the automated inflation/deflation system shown in FIG. 1.

As can be seen in FIG. 2, in a currently preferred embodiment, the control switch unit 20 comprises a separate pressure sensitive switch 43 for inflation and an identical pressure sensitive switch 45 for deflation. A third pressure sensitive switch 47 is provided which initiates a very rapid deflation of the balloon 40. Tactile feedback is provided by indentations in the outer surface of each switch so that each switch can be identified without the user actually looking at the control switch unit. The control switch unit 20 may also embody a display 25 for displaying at least inflation fluid pressure and the elapsed time of inflation and deflation.

When inflation switch 43 is activated, the system is pressurized at a rate that is predetermined by the physician. The invention also contemplates, however, an inflation switch 43 that is pressure sensitive so that the harder it is pressed the higher the inflation pressure in the system. Thus, the physician has more control of the rate of inflation pressure and hence the time it takes to inflate balloon 40.

Several methods of communication between control switch unit 20 and motor drive unit 12 may be utilized. In a currently preferred embodiment for example, such communication is by utilizing an electrical cable 44 routed inside or embedded in the wall of tubing 18 or placed at its surface to connect control switch 20 to motor drive unit 12. Examples of other methods which could be employed include routing the electrical cable 44 separately from the tubing, and the use of electromagnetic waves, including particularly those in the infrared range, for communication between control switch unit 20 and motor drive unit 12.

In order to monitor the pressure inside the balloon 40, a pressure transducer 22, which in the presently preferred embodiment is a piezoresistive transducer sensitive to changes in pressure, is positioned in the system so that it is in fluid communication with the inflation fluid. The currently preferred position for pressure transducer 22 is shown in FIG. 1 at or near the distal end of the syringe 14 and the proximal end 30 of tubing 18, and in communication with the inflation fluid therein. Other types of pressure transducers may be used, as well as other locations of placement of the pressure transducer 22. For example, a force transducer (not shown) may be placed in line with arm 26 of motor drive unit 12 to measure the force it exerts on plunger 16 of fluid chamber 14. This force could be converted by appropriate means into a measurement of the pressure of the inflation fluid. Another example positions the pressure transducer in the display unit.

A signal indicative of balloon inflation fluid pressure as measured by pressure transducer 22 is directed via an electrical connection, including connector 50 to a microprocessor (not shown). The microprocessor can be incorporated in the display unit 24 for example, and the microprocessor processes the signal from the pressure transducer and sends a pressure signal to the display 24 which displays it in analog and/or analog and digital format. The microprocessor could alternatively be associated with, and incorporated within, the electromechanical drive unit 12, or the control switch unit 20.

In addition, a signal indicative of the movement of motor drive unit 12 or plunger 16 is directed to the microprocessor 62. In a currently preferred embodiment a tachometer (not shown) is coupled to the drive motor of electromechanical drive unit 12 to provide a signal indicative of motor speed. Alternatively, a disk could be coupled to the drive motor output shaft which disk is configured to be monitored optically for rotation. The motor speed signal is used by the system for a number of monitoring tasks discussed below. For example, at the start of each inflation and deflation cycle the start of the motor is noted and a time signal is provided to display unit 24 which displays the elapsed time so that the physician can monitor the duration of each inflation. In one embodiment, the timer will begin timing the inflation cycle when inflation switch 43 is released and the pressure in the balloon has reached a preselected value. The timer stops timing when the pressure in the balloon reaches zero or some other preselected value.

Moreover, as will be discussed in more detail below, the motor speed signal can be used in conjunction with the inflation fluid pressure signal sent by the pressure transducer 22 to detect abnormal conditions. For example, if the motor is not moving but there is a rapid decrease in inflation fluid pressure a rupture in the catheter 36 or balloon 40 may be indicated and the microprocessor 62 will trigger an alarm. Also, if the motor is rotating, but there is no change in pressure, or a change in pressure of much less than would be expected, this may also indicate an error condition such as a rupture in the system, and the microprocessor would also trigger an alarm in that case.

When the physician presses the inflation switch 43 or the deflation switch 45 of the automated system 10 according to the invention, the electromechanical drive unit 12 begins pressurizing or depressurizing the balloon 40 of the catheter 36 at a preselected rate, by movement of the plunger 16 by the movable arm 26 actuated by the motor. During the time one of these control buttons is pressed the system maintains the rate of change of pressure in the balloon at a desired level by using a closed-loop feedback control. When the physician releases the switch the motor is stopped. In this way the balloon will always inflate at the same preselected rate, and deflate at the same preselected rate, regardless of individual catheter volume or compliance characteristics.

Also, the physician retains complete control of the inflation and deflation process, as inflation and deflation are manually actuated by pressing appropriate switches of the control switch unit 20. Also, vessel compliance can be monitored by observing the inflation fluid pressure display. The pressure may drift downwardly after the motor of the electromechanical drive unit 12 is stopped due to compliance in the tubing or inflation balloon. The physician increases, decreases or maintains the pressure at some desired value by means of the control switch unit 20.

In an alternative embodiment the system can be configured such that inflation pressure is held constant when the control switch 20 is not activated. When the physician is not activating the control switch to inflate or deflate the balloon, the rate of change of pressure is conformed to a zero value, and the controller compensates for pressure drift due to factors such as tubing 18 and balloon 40 compliance and vessel compliance, to hold the rate of change of pressure at zero. As a result, the pressure in the catheter balloon is held constant when the switch is not activated for inflation or deflation.

In a currently preferred embodiment a user can rapidly deflate the balloon by pressing the rapid deflation control switch 47. This feature operates just as the deflation control switch 45, but the rate of pressure decrease during deflation is very rapid and is conformed to a rapid set point value stored internally.

As a safety feature, plunger 16 is designed to enable the physician to manually grasp it for retraction, thereby rapidly deflating balloon 40. As another safety feature, fluid chamber 14 is designed so that the physician may manually remove it from the system and rapidly deflate balloon 40. Such actions for manual deflation of the balloon may be necessary in various situations such as a power failure.

The rates of change of pressure at which the automated inflation/deflation system 10 inflates and deflates the inflatable balloon member 40 of the catheter 36 using the regular inflation switch 43 and deflation switch 45 can be made the same or can be made to be individually preselected by a user. The system in a currently preferred embodiment has a "set-up" mode. In this mode a user, such as the physician performing the procedure, can input a rate of change of pressure. In one embodiment which will be discussed henceforth, two individual values for rate of change of pressure for both inflation and deflation can be entered. In this "set-up" mode various menu items can be selected by use of "soft" keys 48 on display unit 24. "Soft" keys are programmable keys that have different functions at different times, varying with and depending on the particular menu or prompts displayed according the programming of a microprocessor controlling the system 10. Rate of change of pressure values can be displayed and selected by use of these "soft" keys in accordance with a set-up routine and appropriate menus. Alternatively, values for rate of change of increasing pressure and rate of change of decreasing pressure can be shown on scrolling displays, where each display is scrolled to the particular value desired and then a soft "enter" key included in soft keys 48 is pressed to select the value. As will be apparent to one skilled in the art, any of a number of ways currently well known for entering data needed to initialize the system could be used, including separate switches or dials.

The capability to select a rate of change of pressure can be especially useful in certain specialized procedures, such as those that utilize catheters having a perforated or other specialized type of balloon for delivery of drugs to the site of the stenosis. Such a system of drug delivery requires great control over the balloon pressure in order to enable the operator to control the rate of the delivery of drugs into the blood vessel.

As will be apparent from this generalized description, from a physician's point of view, the automatic inflation system is very easy to use. She simply inflates or deflates the balloon to the desired pressure by means of the control switch unit 20. The rate at which the pressure changes is controlled by the system, and is conformed to the selected value entered previously in the "set-up" mode. Consequently, differences in individual catheter volume and compliance characteristics are automatically compensated for, and all the physician need be concerned with in terms of the inflation aspect of the procedure is the duration of the inflation and the pressure of the balloon, which the physician reads directly from the display 24. This greatly simplifies the physician's task during inflation and deflation cycles of catheterization procedures and makes more uniform and predictable results possible.

Figure 3:
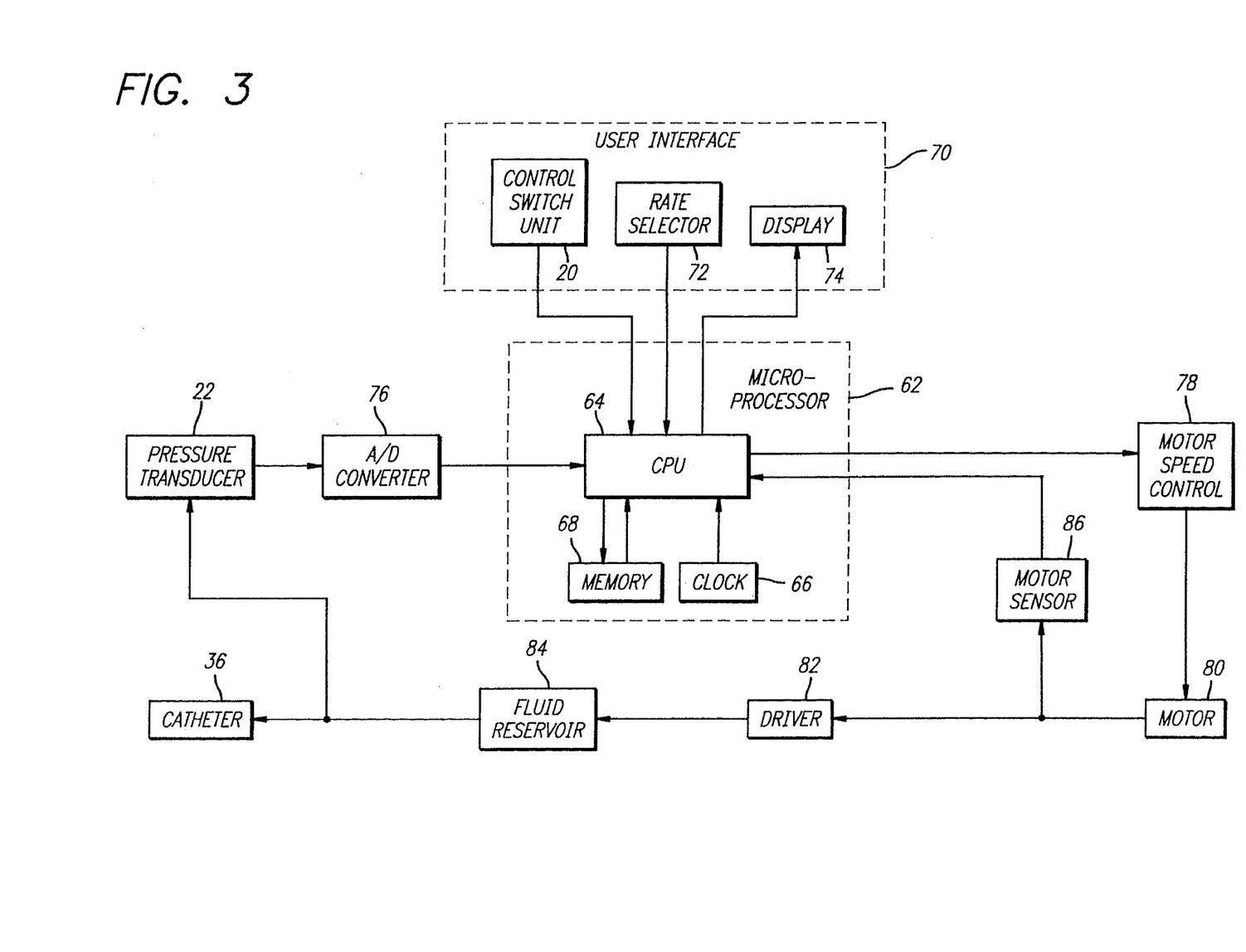
FIG. 3 is a functional block diagram which schematically illustrates the primary components of the presently preferred embodiment of the electronic circuit of the controller of the invention.

Referring to FIG. 3, The interaction of the relevant components of the automated inflation/deflation system 10 specifically for control of the rate of change of pressure are schematically represented. These relevant components comprise a motor control system 60. In a preferred embodiment, the control system incorporates a microprocessor 62. The microprocessor includes a central processing unit (CPU) 64 which interacts with an oscillator or other clock means 66, and memory 68 containing programming for the system, and data registers for storing data used by the central processor in operation of the system. As will be apparent to one skilled in the art, the memory 68 will include both read-only memory (ROM) and random access memory (RAM).

The motor control system 60 also includes a user interface 70, which in the currently preferred embodiment includes: the control switch unit 20; inflation and deflation rate selection means 72 (which comprises a "soft" keypad 48 and accompanying software, but can alternatively be selector dials for inflation and deflation respectively, for example); and, a display 74, which in a currently preferred embodiment is a cathode ray tube (CRT) screen incorporated in display unit 24 and a liquid crystal display 25 incorporated in the control switch unit 20.

The microprocessor 62 interacts with the user interface 70 in the set-up mode to receive and store set-point values for the rates of change of pressure for inflation and deflation as before described. Also, the microprocessor interacts with the user interface to display current values of inflation fluid pressure, time of inflation, and other information helpful to a user. Control switch unit 20 of the interface, of course, interacts with the microprocessor to inflate or deflate the balloon or other inflatable member (not shown) of catheter 36 as the physician using the system desires.

The microprocessor 62 reads pressure data from the pressure transducer 22 in fluid communication with the expandable member (not shown) of the catheter 36. In doing this, an electrical signal produced by the transducer (which may be amplified as needed) is converted to a digital format by an analog to digital converter 76. This data is used by the microprocessor to update the display 74 and to control the rate of pressure change.

The microprocessor 62 also interacts with a motor speed control circuit 78. The preferred operation of motor speed control circuit 78 is to operate motor 80 in a digital format so that motor 80 is either fully on or shut off. Motor 80 generally is on for only a few milliseconds and then turned completely off for a few milliseconds, depending on the requirements governed by the feedback control loop. Alternatively, motor 80 can operate on an analog signal in association with a conventional voltage controller (not shown).

The motor speed control circuit is conventional, and responds to an error signal produced by the microprocessor by appropriately varying the speed of the motor 80 incorporated in the electromechanical drive unit 12. Varying the speed, and when needed, the direction, of the motor affects the motion of a fluid reservoir driver 82. As before mentioned, in a currently preferred embodiment the motor thus controlled is releasably connected to the a plunger 16 within a fluid chamber 14 by a movable arm 26. In this embodiment the reservoir driver would comprise the moveable arm and plunger. The chamber 14 of the currently preferred embodiment corresponds to a fluid reservoir 84, which in turn is fluidly connected to the catheter 36. Motion of the fluid reservoir driver powered by the motor, causes inflation fluid to be injected or withdrawn to or from the catheter to control pressure in the inflatable member 40.

A motor motion sensor 86 is associated with the motor 80. As mentioned, in a preferred embodiment the motor motion sensor is a conventional tachometer device. This motor motion sensor is electrically connected to the microprocessor 62 and indicates motor function, such as rotation or stasis, to the microprocessor.

Figure 4:
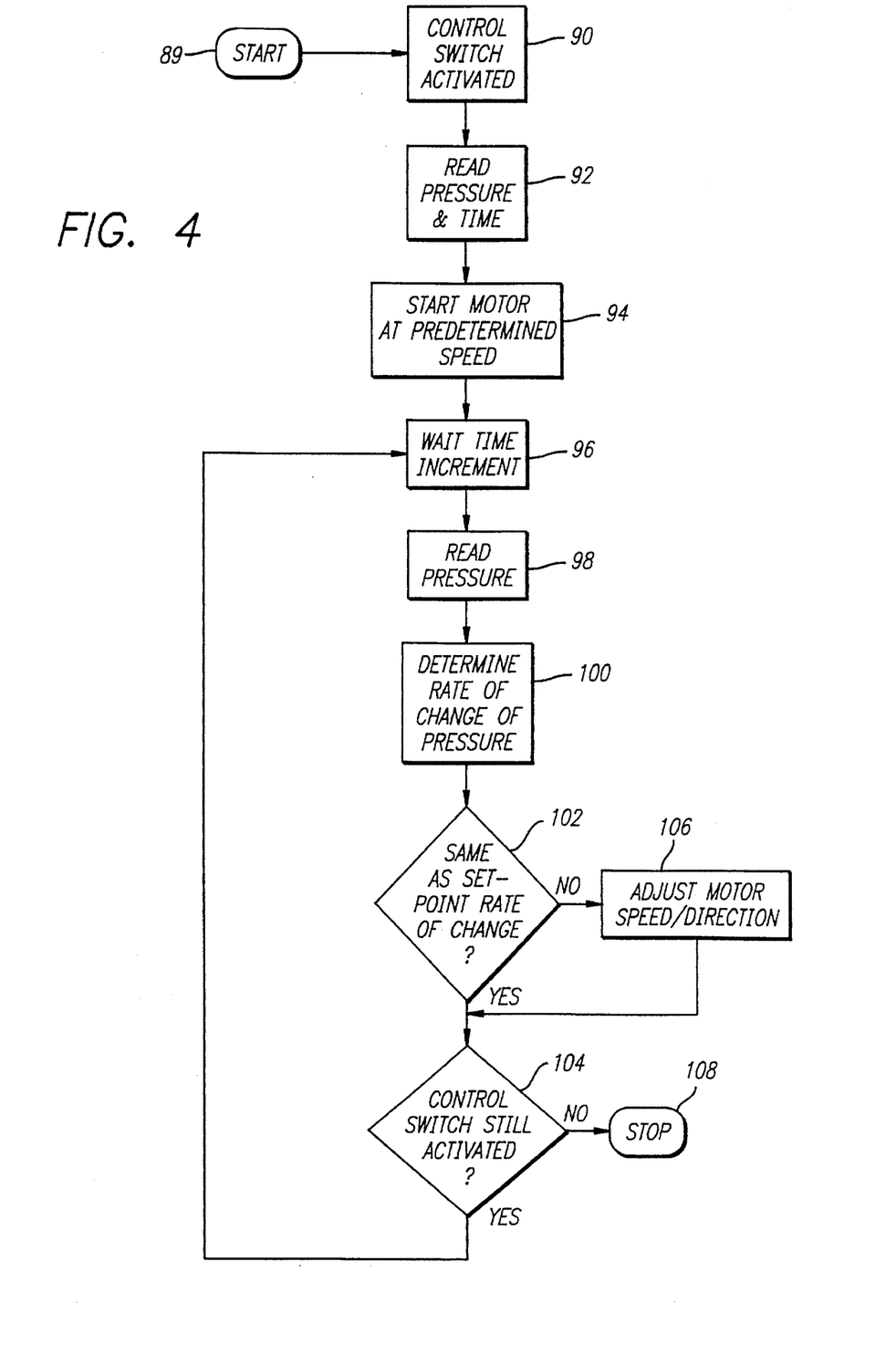
FIG. 4 is a flowchart showing one generalized method of controlling the rate of change of pressure according to the invention.

Referring to FIG. 4, the overall method of controlling the rate of change of pressure in the inflatable member 40 of the catheter 36 is shown in flowchart form. At a starting point 89, an inflation or deflation is started in response to actuation of the inflation 43, deflation 45, or rapid deflation 47 switch of the control switch unit 20 at step 90 by the physician user. Next, in step 92, the fluid pressure sensed by the pressure transducer 22 is initially read, and the time is read from the clock 66. It is intended that the pressure read at step 92 be associated with a starting time. The system 60 will thereafter monitor and control the motor speed at predetermined time increments as discussed below. Then, at step 94 the motor 80 is started in the appropriate direction, forward or backward depending upon which switch is actuated, at a particular initial speed determined by the programming of the microprocessor 62.

The initial speed is based on several parameters. If either of the inflation 43 or deflation 45 switches of control switch unit 20 are actuated, the initial speed is based partly upon the set-point rate of change of pressure value for inflation or deflation, as may be appropriate, entered by a user during a set-up procedure earlier. If the rapid deflation switch 47 is actuated, the initial speed is based partly upon a preprogrammed relatively very rapid speed. In addition to these values, the presently sensed pressure value is also taken into account in determining the initial speed of the motor. As is known in the art from experience with manual inflation devices, at relatively high pressures only a small displacement of the plunger 16 will produce a large pressure change. Whereas at relatively low pressures, and particularly when the balloon 40 is not completely inflated, a relatively large displacement of the plunger does not produce a commensurate change in pressure due to compliance characteristics. Therefore, the same motor speed will produce different rates of change of pressure at different starting pressures. Thus the initial speed at which the motor is started is determined using an algorithm stored in the microprocessor that takes into account both the effect of the catheter compliance characteristics at the starting pressure and the preselected rate of change of pressure entered by the physician earlier or the rapid deflation rate stored in the microprocessor in the case of actuation of the rapid deflation switch 47.

Due to these considerations the speed at which the motor begins is calculated to give approximately the set point rate of change of pressure at the current sensed pressure (or a predetermined very rapid rate of change of decreasing pressure at the sensed pressure if the rapid deflation switch is actuated) but an additional factor is considered. This calculated initial speed is based on average values of catheter inflation fluid volumes and compliance parameters for the various sizes and types of catheters expected to be used with the system. As different sizes and types of catheters will be used with the system an empirical "best fit" is used in the programming to give the best approximation of the initial speed required at the sensed pressure over this range of different catheters expected to be used with the system.

It is also an embodiment of the invention to provide a rapid deflation mode that simply supplies full current to the motor to cause the plunger to deflate the system almost instantaneously. For example deflation switch 47 can be adapted so that when pressed it causes full current to be sent to motor 80 so that plunger 16 almost instantaneously withdraws fluid from the system to a predetermined amount such as 1 atmosphere or less.

As will be apparent to one skilled in the art, an alternative embodiment could be to simply start the motor at a single preselected speed regardless of these factors. Since the motor speed control system 60 would quickly conform the rate of change of pressure to the appropriate set point value, this may be possible. However, particularly at high pressures, an undesirable pressure spike may result upon starting the motor using such a control system. At low pressures there could be an unacceptable lag in inflation due to the motor starting at too slow a speed.

Alternatively, in another embodiment, the initial motor speed can be made to be simply a function of sensed pressure, which would reduce the probability of an unacceptable pressure spike. While not ideal, this method allows reduced complexity in programming.

Next, after starting the motor 80 at the initial speed, at step 96 the control system 60 then waits a predetermined time period before reading the inflation fluid pressure at step 98 for comparison with the previously sensed pressure. In a currently preferred embodiment this time increment is 100 milliseconds. At step 100 the rate of change of pressure is then determined by the microprocessor 62, by dividing the difference of the current sensed pressure and the previous pressure read from the transducer 22 by the applicable time increment (100 milliseconds for example). This determined rate of change of pressure is then compared at step 102 with the set-point rate of change of pressure preselected by the user during set-up, or the preprogrammed very rapid deflation value, as appropriate, depending on which control switch 43, 45, or 47 of the control switch unit 20 is actuated. If the rate is found to be correct, within predetermined error limits, the programming then determines at step 104 if the control switch previously activated is still activated. If the same switch is still actuated the program loops back to step 96 wherein the system waits the predetermined time interval and repeats the above steps after step 96 sequentially as before.

If the rate of change of pressure is not found to be correct within the preset error limit at step 102 then the program branches to step 106. At step 106 the motor speed, and even direction if required, is adjusted by the control system 60 to conform the rate of change of pressure to the preselected rate of change of pressure.

If at step 104 the control switch actuated previously is not now actuated, then the motor is stopped at step 108. The activation of a control switch of control switch unit 20 restarts the control process. Whether the motor 80 is activated or not the pressure is monitored and a pressure display is continuously updated.

As can be appreciated by one skilled in the art, the forgoing description of the method is very general, and numerous different ways of carrying out the particulars of the method will suggest themselves. For example, the conformance of the rate of change of pressure involved at step 106 can be carried out by first determining the magnitude and sense of the error in the rate of change of pressure determined found at step 102. The microprocessor 62 then generates an error signal indicative of the magnitude and negative or positive sense of the error in rate of change of pressure. This error signal is sent to the motor control circuit 78 which adjusts the speed, and, if necessary, the direction of the motor in a conventional manner.

Also, in an alternative embodiment, at step 104, if it is found that the control switch is not activated instead of stopping the motor as in step 108, the rate of change of pressure could instead be conformed to a zero rate. This would have the effect of holding the pressure at the current value when the switches 43, 45, and 47 of the control switch unit 20 are not activated. This can be done for example by repeating steps 96 through 106 of FIG. 4, using the zero value to compare the determined rate of change of pressure to, instead of the preselected values or the internally stored rapid deflation rate. In certain situations, some physicians may prefer holding the rate of change of pressure at zero to simply stopping the motor when the control switch unit is not activated, an allowing the pressure to degrade.

Figure 5A:
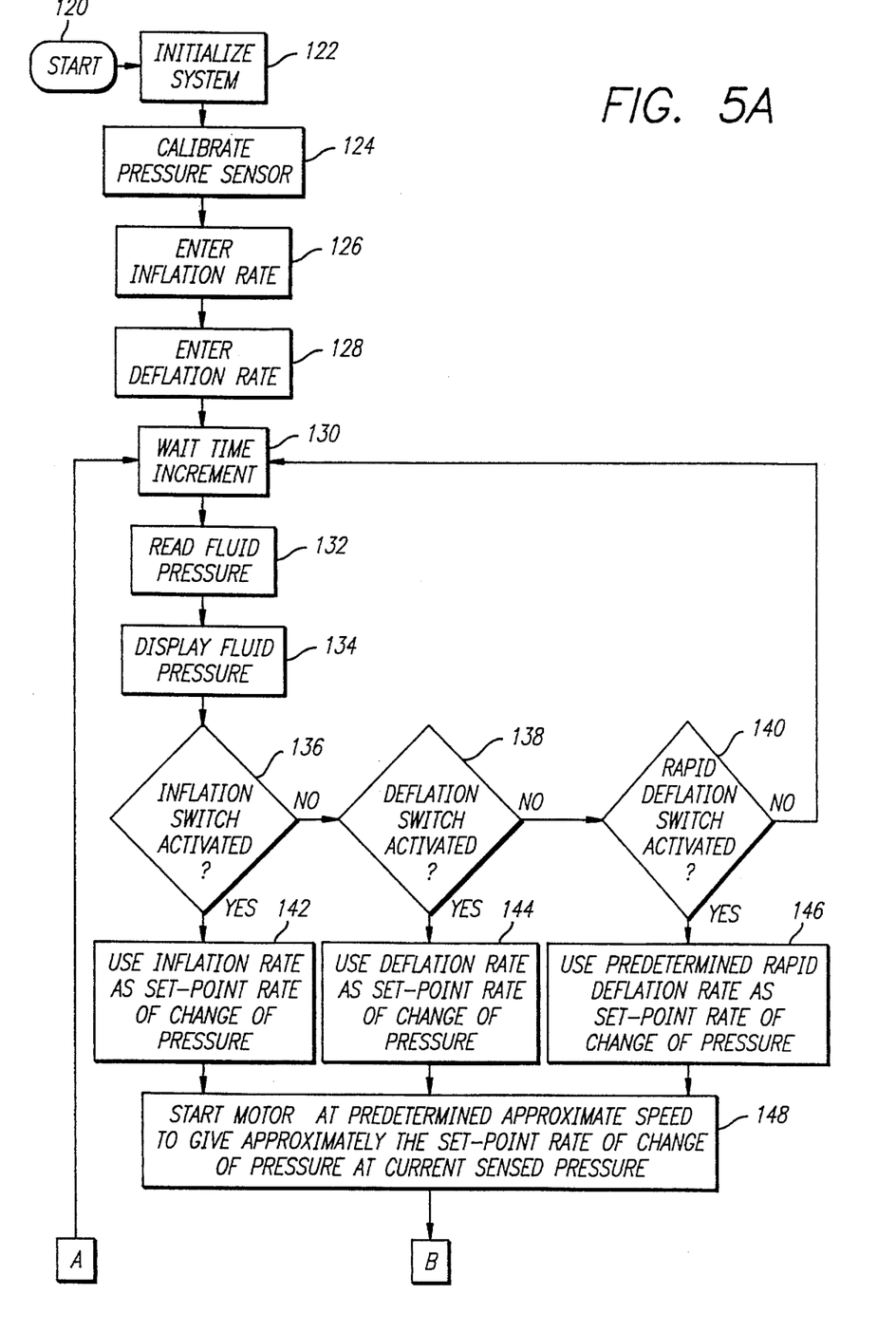
FIGS. 5a and 5b are a flowchart showing one presently preferred method for programming the digital microprocessor of the electronic circuit of the controller of the invention.
Figure 5B:
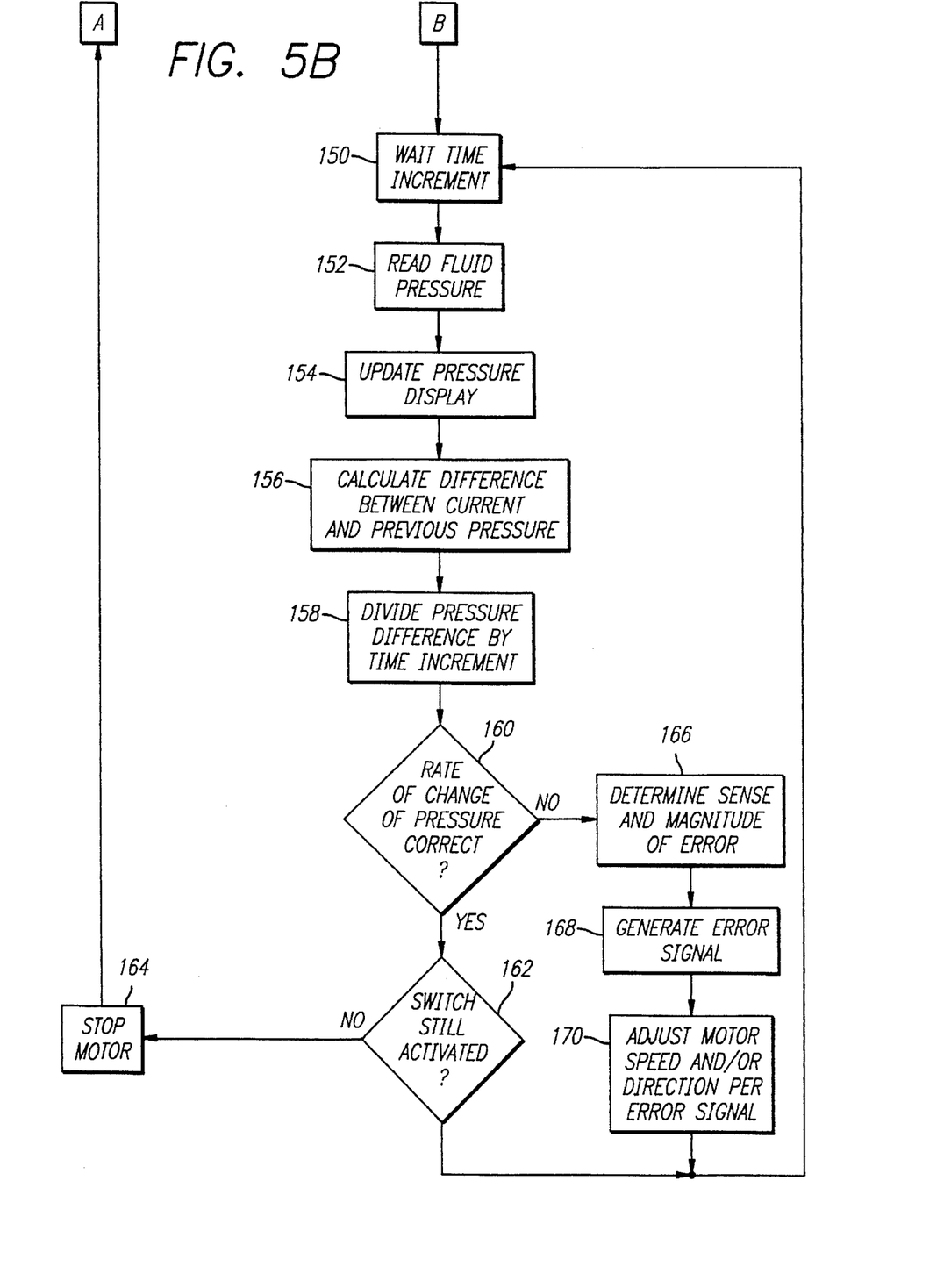

Referring now to FIGS. 5*a* and 5*b*, a flowchart of an exemplary more detailed method of controlling the rate of pressure change within the inflatable member 40 of the catheter 36, representing a way of programming the microprocessor 62 in this regard, is shown. At the start 120 the system initializes itself at step 122, including self-diagnostic tests, and at step 124 calibrating the pressure sensor 22. This calibration is done with reference to atmospheric pressure in a conventional manner. A user can be prompted for, and enter data, for example a preference for the units of a pressure display, pounds per square inch (PSI) or atmospheres (ATM). The system can be provided with an alarm feature, wherein an alarm will sound if a preselected pressure is exceeded, and the system may prompt for this alarm to be enabled or not, and for this alarm threshold pressure value if enabled. The system can also prompt for and allow a user to enter inflation and deflation rate of change of pressure values at steps 126 and 128 respectively. Alternately, one rate for both inflation and deflation could be employed. In a currently preferred embodiment this is done by displaying possible rates and allowing the user to select a desired rate by scrolling and selecting from the displayed values using the "soft" keys 48. The entry of this data can be done in a set-up mode for example, prior to beginning the procedure as before discussed.

In operation, the system programming causes the output of the pressure sensor 22 to be read at step 132, the displays 24 and 25 to be updated at step 134, and control switches 43, 45, and 47 to be monitored for actuation at steps 136, 138 and 140 every 100 milliseconds. One hundred milliseconds is the time increment in step 130 in the presently preferred embodiment. Therefore, steps 130 through 140 constitute a monitoring loop that is followed by the program as long as no switch is actuated. This has the effect of monitoring current pressure and displaying it for the user. This pressure and switch monitoring loop is continuous both before and after a period of actuation of any of the switches on control switch unit 20.

If a switch 43, 45, or 47 of control switch unit 20 is actuated this is detected at step 136, 138, or 140o At steps 142, 144, and 146 the appropriate one of the set point rate of change of pressure values entered earlier is loaded from memory, depending on which of the three switches is activated, to an active memory for use by the program. If the inflation switch 43 is actuated the set point rate of change of pressure used is the inflation rate entered earlier at step 126. Likewise, if the deflation switch 45 is actuated, the deflation rate entered at step 128 is used. If the rapid deflation switch 47 is activated, then the rapid deflation rate of change of pressure is used. As before mentioned, this rapid deflation rate value is contained within the programming or microprocessor memory, and in a presently preferred embodiment is not user defined.

The programming of the microprocessor then conforms the rate of change of pressure to this stored value in a conventional manner by feedback loop control. This is done for example in steps 148 through 170 of FIGS. 5*a* and 5*b*, looping back to step 150 to repeat. In the illustrated embodiment at step 148, the motor is started in the proper direction and at the appropriate speed as calculated based upon the set point rate of change of pressure and the current pressure as before described in connection with FIG. 4. The system then waits one hundred milliseconds, or some other predetermined time interval, and then samples the fluid pressure again at step 152. Again this involves reading the pressure from the sensor 22. Then, at step 154 the pressure display 24 is updated. This provides a user with a continuously updated display of fluid pressure. Next, the rate of change of pressure is determined at steps 156 and 158 by comparing the current pressure reading to the previous pressure reading taken one hundred milliseconds before, and dividing by one hundred milliseconds. As before mentioned, another time increment can be used, so long as the time increment is used consistently both in the interval of sampling the pressure and in calculating the rate of change of pressure.

In one embodiment of the invention, the calculated rate of change of pressure is compared to the set point rate at step 160. Depending on the outcome of the comparison, the program branches at that point. If the rate of change of pressure is correct within predetermined limits the program moves on to step 162 where if the switch (43, 45, or 47) of control switch unit 20 is still actuated the program repeats, looping back to step 150 to again monitor the rate of change of pressure over the next time increment. If the switch is found to be no longer activated, then at step 164 the motor is stopped and the program branches back to step 130 and enters the loop for monitoring and displaying the pressure every time increment, and monitoring the switches for a new activation of one of them (43, 45, or 47). As will be apparent to one skilled in the art, step 162 can be placed anywhere in the sequence between step 150 and the illustrated position of step 162. It can be appreciated by those skilled in the art that various other methods of calculating the rate of change of pressure variations exist and do not depart from the spirit and scope of the invention.

At step 160, if the rate of change of pressure is not found to be correct within predetermined limits, then the program branches to correct the rate of change of pressure by adjusting the motor speed of the electromechanical drive unit 12. As is known in the art, there are numerous methods for adjusting the motor speed to bring the pressure reading back within limits. One method is to first calculate the magnitude and sense (too fast or too slow) of the error in rate of change of pressure at step 166. Next, at step 168, an error signal is generated which is a function of the magnitude and sense of the error. This signal is sent to the motor speed control circuit 78 which adjusts the speed of the motor of the drive unit 12 accordingly. Also, the direction of the motor can be changed, if required, in conforming the rate of change of pressure. After the motor speed is adjusted at step 170, and the program returns to step 150 to repeat the process at the next time increment.

In this way the rate of change of pressure within the inflation lumen and inflatable member 40 of the catheter 36 is held constant at the appropriate set point rate whenever a control switch 43, 45, or 47 of the control switch unit 20 is activated. The motor stops when no switches are activated. The inflation fluid pressure is monitored and displayed throughout, whether a switch is actuated or not, with the display being updated every 100 microseconds.

As will be apparent to one skilled in the art, the programming can be easily modified as before discussed to cause the system to hold the rate of change of pressure at a zero value when no switches are activated. This would have the effect of holding the pressure at the current level by the same feedback loop control means that controls the rate of change of pressure during an inflation or deflation. Thus the system 10 can be made to hold a vacuum while the catheter is being maneuvered to the stenosis for example, or will hold the selected pressure upon release of the control switch after inflation. Pressure within the balloon can then be again altered after the desired time by activation of the control switch to inflate or deflate the balloon as appropriate.

Figure 6:
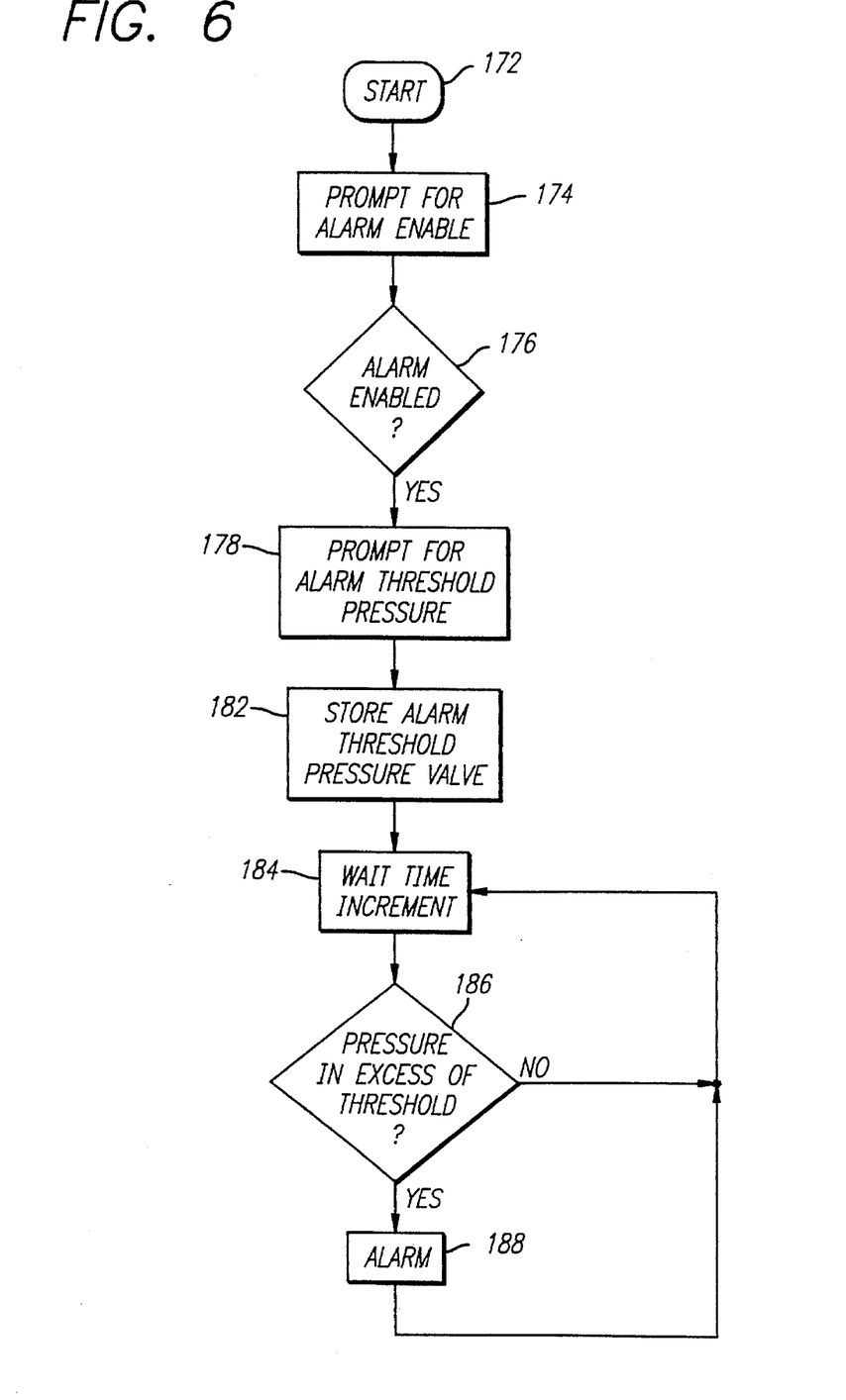
FIG. 6 is a flowchart showing a presently preferred method for programming a digital microprocessor of the invention.

In a presently preferred embodiment, the system also has a high pressure alert that is activated at a preset pressure limit as before mentioned. Referring to FIG. 6, a presently preferred method of providing for such an alert is shown. In the programming of the microprocessor 62, after the system has begun to run at step 172, a prompt at step 174 is provided to a user during a set-up mode of the system 10 to enable the high pressure alert. Selection of alert enablement is done through the "soft" keys 48 for example. If a user has enabled the alert, at step 178 the system prompts for the pressure at which an alert will sound.

If a user does enable the high pressure alert at step 176 and set a pressure at which the alert will sound, for example by scrolling up and down through displayed possible values and selecting the desired value through use of the "soft" keys 48, at step 182 the selected alert threshold value is stored. At steps 184 through 188 the programming monitors the pressure at each time increment of one hundred milliseconds (or some other predetermined increment) and activates an alert if the stored pressure threshold value is exceeded. This is done by comparing the current sensed fluid pressure value to the stored value at step 186 and activating the alert at step 188 if the current pressure is greater than the alert threshold value. The programming then loops back to step 184 to repeat the process. If the current fluid pressure is not greater than the threshold value at step 186 the alert is not activated. Some physicians inflate the balloon to pressures of about 300 to 350 PSI. In these cases, in order to avoid triggering the alert, the physician would set the high pressure alert limit at a value above 350 PSI so the alert is not triggered.

As will be apparent to one skilled in the art this method can be combined with conventional circuitry to provide an audio alert signal to be perceived by the physician using the system 10 during the period of time the pressure is in excess of the threshold value. In response to this audio signal, the physician can alter the pressure by pressing the deflation switch 45 or rapid deflation switch 47. Of course the physician could also reduce the pressure by releasing the syringe pump from the drive means as before described. In this way numerous safeguards can be employed to assure that a preset maximum pressure will not be exceeded accidentally, and that the physician can reduce pressure if required.

As will be apparent to one skilled in the art, in an alternate embodiment the control system 60 could be programmed to stop the motor 80 when the preselected maximum pressure threshold is reached. This could be in lieu of, or in addition to activating of high pressure alert. An override feature can be incorporated in such a system to allow a physician to exceed the maximum pressure limit if desired.

The system in a currently preferred embodiment also provides for an alarm when an abnormal pressure condition exists, such as would be occasioned by a balloon 40 rupture. Rotation of the motor 80 is monitored as before mentioned by use of a tachometer, as is the rate of change of pressure. As mentioned, if, for example, the motor is not moving, but there is a rapid decrease in fluid pressure, or the motor is moving in a direction that should cause inflation, but the pressure does not increase, this may indicate a serious problem such as a rupture.

Figure 7:
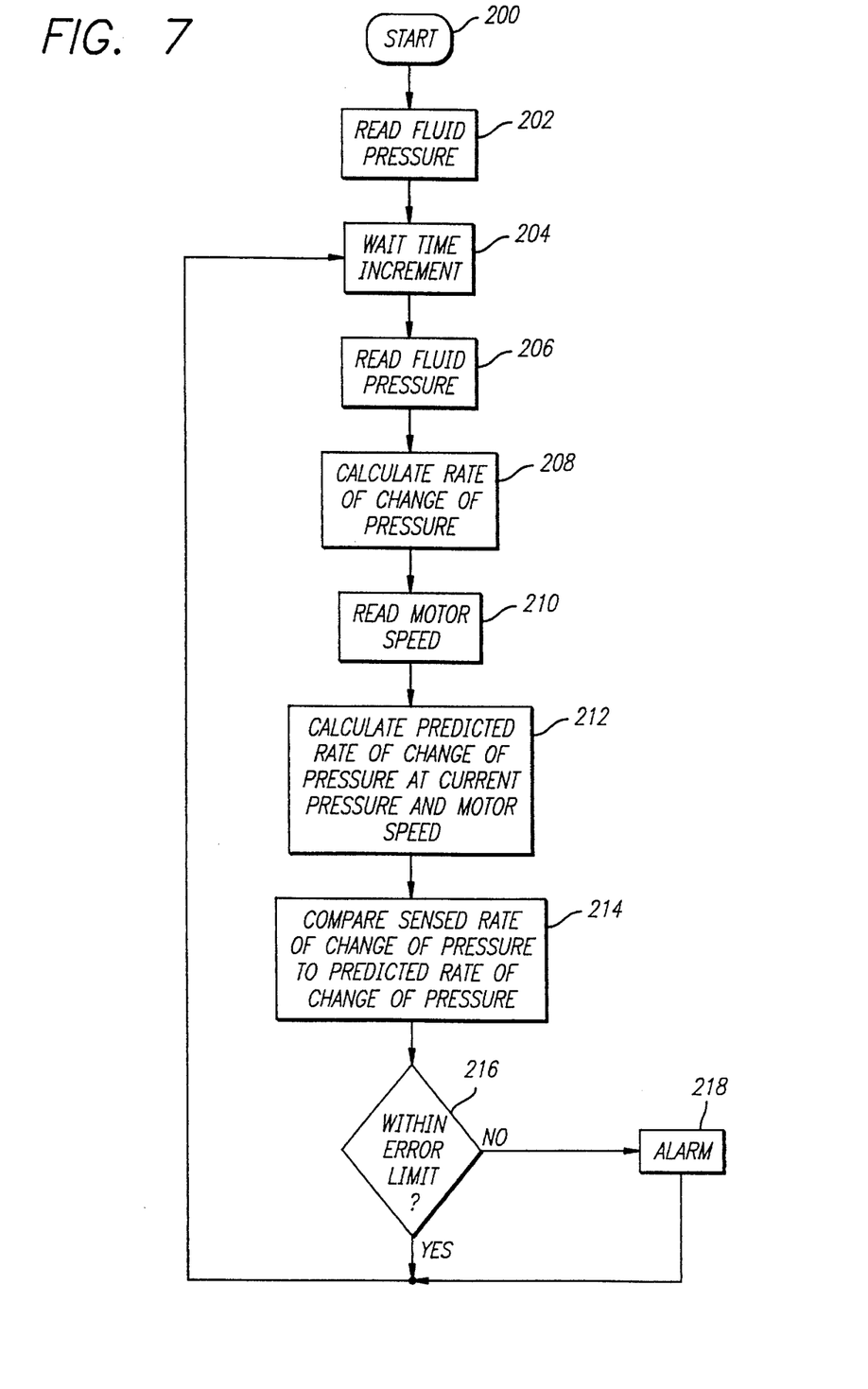
FIG. 7 is a flowchart showing a presently preferred method for programming a digital microprocessor of the invention.

Referring to FIG. 7, a method of monitoring the inflation system 10 for such an abnormal pressure condition is shown. Starting at step 200, the fluid pressure is read at each time increment, which again is 100 milliseconds in the currently preferred embodiment. Thus, at step 202, the fluid pressure sensed by the pressure transducer 22 is read by the microprocessor 62, and at step 204, the predetermined time increment is allowed to pass, and at step 206, the fluid pressure is read again. The rate of change of pressure is then calculated at step 208 by the microprocessor.

The speed of the motor 80 is also sensed once each time increment by reading and interpreting the output of the tachometer or other motor speed sensor 86 at step 210. After reading the motor speed the microprocessor calculates at step 212 a predicted rate of change of pressure at the current pressure and motor speed. This calculated predicted rate is based on a preprogrammed rate curve based on empirical data for typical catheters at various pressures and motor speeds. At step 214 the actual sensed rate of change is compared to the predicted rate of change of fluid pressure for the current sensed pressure and motor speed. At step 216 if this comparison shows the two rates are the same within a predetermined error limit the programming of the microprocessor 62 repeats the process at the next time increment, looping back to step 204. If the rate of change of pressure is not within the predetermined error limit an abnormal pressure condition is indicated and at step 218 and an alarm is sounded. The programming then loops back to step 204 to monitor these same parameters. The alarm is given an activation signal at every time increment (100 milliseconds, or some other predetermined value) and as before discussed in connection with the maximum pressure alert will continue to sound until the abnormal pressure condition is corrected as sensed by this monitoring loop program, or the power is turned off.

In this way a physician using the system 10 will be alerted whenever there is a leak, or an obstruction, or a balloon rupture in the system, or any other problem that would cause the pressure to depart significantly from a predicted response to actuation of the electromechanical drive unit 12.

Thus, by means of the above described systems 10 and 60, in normal operation, a physician will be able to inflate and deflate an inflatable member 40 of a catheter 36 simply by means of actuation of switches 43, 45, and 47 located conveniently on a control switch unit 20 adjacent the proximal end 38 of a catheter 36. Inflation and deflation will take place at a predicable user selected rate, regardless of the volume and compliance characteristics of the particular catheter used. As the balloon is inflated, deflated or when the motor of the electromechanical drive unit 12 is stopped, the physician can monitor the fluid pressure within the balloon 40 by reference to the displays 24 and 25. In a currently preferred embodiment a user can monitor body lumen compliance by observing pressure drop within the system when the user releases the controls of control switch unit 20 at the desired inflated pressure for a selected period of time.

Typically after inflation for a few seconds the inflation fluid pressure is then reduced to allow blood to flow past the stenosis site, and a vacuum may be applied to the balloon to reduce as much as possible the profile of the catheter to aid this blood flow. The balloon may be inflated and deflated a number of times during a procedure, as this allows more accumulated inflation time, but reduces the length of time the blood flow distal of the stenosis is cut off in any instance of inflation, with a corresponding reduction in ischemia that would otherwise result if a single longer inflation were used for example. This is very easily accomplished using the system 10 of the present invention.

As mentioned, a timer can be incorporated in the system which will display the time of inflation on the display. This time display can be made to begin for example at the initiation of each inflation. The timer can be made to stop for example when each deflation is begun after an inflation. The timer would then automatically reset for the next inflation. In another embodiment, a display of accumulated inflation time could be provided. The time display is controlled by the microprocessor 62.

Using the automated inflation/deflation system 10 of the invention to inflate and deflate and collapse an inflatable member 40 of a connected catheter 36 is a simple procedure. The physician simply activates deflation switch 45 or rapid deflation switch 47 of the control switch unit 20 and watches the pressure drop, releasing the selected control switch when the pressure has dropped to the desired value. The desired value can of course be a negative pressure value thereby creating a vacuum. In a currently preferred embodiment the electromechanical drive unit 12 is made to be able to draw slightly less than one atmosphere vacuum. Thus the motor will stop and no further vacuum will be applied when that negative pressure value is reached.

From the above, it is evident that the present invention provides for an advantageous design in which an inflation/deflation system can be operated with ease by a physician at the same time she is maneuvering a dilatation catheter inside the patient's vasculature. The invention provides for precise control and display of inflation times and pressures, and several safety features for alerting a user to undesirable conditions such as too high a fluid pressure and balloon rupture, and provides for rapid deflation of the balloon catheter. While several particular forms of the invention have been illustrated and described, it also will be appreciated that various modifications can be made to the present invention without departing from the spirit and scope thereof.

What is claimed is:

1. An automatic inflation device for a catheter system for use in a body lumen of a patient, comprising:

a catheter having a proximal end and a distal end, and an inflatable member near said distal end;

an inflation lumen within said catheter for providing fluid communication between said proximal end and said inflatable member;

a pump adapted to pressurize fluid in said inflation lumen and said inflatable member, said pump having an associated movement speed and movement directions;

a pressure sensor adapted to measure fluid pressure in said inflatable member; and a controller adapted to be programmed with a selected rate of fluid pressure change, that receives the measured pressure sensed by the pressure sensor and determines the actual rate of pressure change therefrom, that compares the actual rate of pressure change to the programmed selected rate of change and determines the difference, and that controls the speed of the pump to decrease said difference, whereby said inflatable member is inflated by fluid pressurized at the selected rate of pressure change.

2. The automatic inflation device of claim 1, wherein the controller conforms the rate of change of fluid pressure during deflation to a user selectable rate of change of pressure.

3. The automatic inflation device of claim 1, wherein the controller comprises a feedback loop controller.

4. The automatic inflation device of claim 3, wherein the controller employs an analog signal.

5. The automatic inflation device of claim 3, wherein the controller employs a digital signal.

6. The automatic inflation device of claim 1, wherein the controller is adapted to automatically control the pump to maintain a selected programmable pressure and wherein the controller automatically controls the pump movement direction after reaching said selected programmable pressure to maintain said selected programmable pressure.

7. The automatic inflation device of claim 1, wherein the pump comprises a chamber member adapted to contain fluid, the interior of said chamber being in fluid communication with said inflation lumen, and a plunger member cooperating with said chamber member to pressurize the fluid in said chamber member, and a motor adapted to actuate said plunger, said motor being adapted to cooperate with said controller to actuate said plunger at more than one associated speed.

8. The automatic inflation device of claim 1, wherein said control means includes a control switch unit for controlling said powered fluid drive means.

9. The automatic inflation device of claim 1 further comprising:

a pump movement sensor that monitors said pump speed and provides a signal representative of said pump speed;

wherein said controller receives said pump speed signal, compares it to the actual sensed rate of pressure change and provides an alarm based on said comparison.

10. The automatic inflation device of claim 9 further comprising:

a memory in which is stored data concerning various inflatable members;

wherein said controller accesses the memory for data concerning the particular inflatable member at said distal end of the catheter, predicts a rate of pressure change based on the current pump speed, the current sensed pressure, and the inflatable member data, compares the predicted rate of pressure change to the actual rate of pressure change and provides an alarm based on said comparison.

11. The automatic inflation device of claim 1 wherein said controller automatically controls the initial speed of the pump based on the pressure sensed by the pressure sensor.

12. The automatic inflation device of claim 11 wherein said controller automatically controls the initial speed of the pump based on the pressure sensed by the pressure sensor, the selected programmed rate of pressure change, and the compliance characteristics of the catheter.

13. An automatic inflation device for a catheter system for use in a body lumen of a patient, comprising:

a catheter having a proximal end and a distal end, and an inflatable member near its distal end;

an inflation lumen within said catheter for providing fluid communication between said proximal end and said inflatable member;

a pump adapted to pressurize fluid in said inflation lumen and said inflatable member, said pump having an associated movement speed and movement directions;

a pressure sensor adapted to measure fluid pressure in said inflatable member; and a controller adapted to be programmed with a selected rate of fluid pressure change, that receives the measured pressure sensed by the pressure sensor and determines the actual rate of pressure change therefrom, that compares the actual rate of pressure change to the programmed rate of change and determines the difference, and that controls the speed of said pump to decrease said difference, said controller also adapted to automatically control the pump to maintain a selected programmed pressure wherein the controller automatically controls the pump movement direction after reaching said selected programmable pressure to maintain said selected programmed pressure.

14. The automatic inflation device of claim 13, wherein the controller conforms the rate of change of fluid pressure during deflation to a predetermined rate of change of pressure.

15. The automatic inflation device of claim 13, wherein said controller comprises a microprocessor.

16. The automatic inflation device of claim 13, wherein said controller comprises an analog device.

17. The automatic inflation device of claim 13, wherein said controller comprises a digital device.

18. The automatic inflation device of claim 13, further comprising an alarm for alerting a user when a preselected fluid pressure is exceeded.

19. The automatic inflation device of claim 13, further comprising an alarm for alerting a user to an abnormal fluid pressure condition.

20. The automatic inflation device of claim 14, wherein the pump comprises a chamber member adapted to contain fluid, the interior of said chamber being in fluid communication with said inflation lumen, and a plunger member cooperating with said chamber member to pressurize the fluid in said chamber member, and a motor adapted to actuate said plunger, said motor being adapted to cooperate with the controller to actuate the plunger at more than one associated speed.

21. The automatic inflation device of claim 20, wherein the pump comprises a syringe pump.

22. The automatic inflation device of claim 13, wherein said control means includes a control switch unit for controlling said powered pump means.

23. The automatic inflation device of claim 13 further comprising:

a pump movement sensor that monitors said pump speed and provides a signal representative of said pump speed;

wherein said controller receives said pump speed signal, compares it to the actual sensed rate of pressure change and provides an alarm based on said comparison.

24. The automatic inflation device of claim 23 further comprising:

a memory in which is stored data concerning various inflatable members;

wherein said controller accesses the memory for data concerning the particular inflatable member at said distal end of the catheter, predicts a rate of pressure change based on the current pump speed, the current sensed pressure, and the inflatable member data, compares the predicted rate of pressure change to the actual rate of pressure change and provides an alarm based on said comparison.

25. The automatic inflation device of claim 13 wherein said controller automatically controls the initial speed of the pump based on the pressure sensed by the pressure sensor.

26. The automatic inflation device of claim 25 wherein said controller automatically controls the initial speed of the pump based on the pressure sensed by the pressure sensor, the selected programmed rate of pressure change, and the compliance characteristics of the catheter.

27. An automatic inflation device for an angioplasty catheter system for use in a body lumen of a patient, comprising:

a catheter having a proximal end and a distal end, and an inflatable member near its distal end;

an inflation lumen within said catheter for providing fluid communication between said proximal end and said inflatable member;

a syringe pump in fluid communication with said inflation lumen and adapted to pressurize fluid in said lumen and said inflatable member, said syringe pump comprising a motor having an associated motor movement speed and movement directions;

a fluid pressure transducer in fluid communication with said inflatable member, adapted to measure fluid pressure in said inflatable member and produce a pressure signal which is a function of the fluid pressure in the inflatable member;

a motor movement sensor for monitoring said motor movement speed and providing a signal representative of said motor movement speed; and a feedback loop controller adapted to control a rate of change of fluid pressure within the inflation member in accordance with a programmed rate of pressure change by varying the motor speed and direction in response to a rate of change of pressure error signal derived by comparing a measured pressure in the inflatable member at a first sample time and a measured pressure at a second sample time separated by a predetermined time interval, the measured pressure being based upon the pressure signal, said feedback loop controller comparing the rate of change of pressure signal to the programmed rate of change of pressure and generating the error signal whereby said inflatable member is inflated by fluid pressurized at a rate of change of pressure that tracks closely the user programmed rate of change of pressure, wherein said controller receives said pump speed signal, compares it to the actual sensed rate of pressure change and provides an alarm based on said comparison.

28. The automatic inflation device of claim 27, wherein the controller conforms the rate of change of fluid pressure during deflation to said user selectable rate of change of pressure.

29. The automatic inflation device of claim 27, wherein the controller controls the motor direction, and the controller causes the motor to operate at a maximum speed in a reverse direction during deflation to cause substantially instantaneous deflation in the inflatable member.

30. The automatic inflation device of claim 27 further comprising:

a memory in which is stored data concerning various inflatable members;

wherein said controller accesses the memory for data concerning the particular inflatable member at said distal end of the catheter, predicts a rate of pressure change based on the current pump speed, the current sensed pressure, and the inflatable member data, compares the predicted rate of pressure change to the actual rate of pressure change and provides an alarm based on said comparison.

31. The automatic inflation device of claim 27 wherein said controller automatically controls the initial speed of the pump based on the pressure sensed by the pressure sensor.

32. The automatic inflation device of claim 31 wherein said controller automatically controls the initial speed of the pump based on the pressure sensed by the pressure sensor, the selected programmed rate of pressure change, and the compliance characteristics of the catheter.

33. The automatic inflation device of claim 31 wherein said controller is also adapted to automatically control the pump to maintain a selected programmed pressure wherein the controller automatically controls the pump movement direction after reaching said selected programmable pressure to maintain said selected programmed pressure.

* * * * *

UNITED STATES PATENT AND TRADEMARK OFFICE
CERTIFICATE OF CORRECTION

PATENT NO. : 5,599,301
DATED : Feb. 4, 1997
INVENTOR(S) : James M. Jacobs, Joseph A O'Donnell It is certified that error appears in the above-identified patent and that said Letters Patent is hereby corrected as shown below:

Column 18, line 21, claim 20, change "14", to read --13--.

Signed and Sealed this

Fifth Day of September, 2000

*Attest:*

Q. TODD DICKINSON

*Attesting Officer*  *Director of Patents and Trademarks*